(12) United States Patent
Oda et al.

(10) Patent No.: US 12,708,477 B2
(45) Date of Patent: Aug. 18, 2026

(54) MEDICAL IMAGING DEVICE

(71) Applicants: University of Tsukuba, Tsukuba (JP); Yamada Shadowless Lamp Co., Ltd., Tokyo (JP)

(72) Inventors: Tatuya Oda, Tsukuba (JP); Kazuaki Yamazaki, Tokyo (JP); Toshihiro Suzuki, Tokyo (JP); Hiroyuki Urashima, Yashio (JP)

(73) Assignees: University of Tsukuba, Tsukuba (JP); Yamada Shadowless Lamp Co., Ltd., Tokyo (JP)

( * ) Notice: Subject to any disclaimer, the term of this patent is extended or adjusted under 35 U.S.C. 154(b) by 254 days.

(21) Appl. No.: 18/722,091

(22) PCT Filed: Dec. 15, 2022

(86) PCT No.: PCT/JP2022/046236
§ 371 (c)(1),
(2) Date: Jun. 20, 2024

(87) PCT Pub. No.: WO2023/120379
PCT Pub. Date: Jun. 29, 2023

(65) Prior Publication Data

US 2025/0057628 A1 Feb. 20, 2025

(30) Foreign Application Priority Data

Dec. 22, 2021 (JP) ................................ 2021-207878

(51) Int. Cl.
*A61B 90/35* (2016.01)
*A61B 90/00* (2016.01)
*H04N 23/56* (2023.01)

(52) U.S. Cl.
CPC ............ *A61B 90/35* (2016.02); *A61B 90/361* (2016.02); *A61B 90/37* (2016.02); *H04N 23/56* (2023.01)

(58) Field of Classification Search
CPC ....... A61B 90/35; A61B 90/361; A61B 90/37; H04N 23/56
See application file for complete search history.

(56) References Cited

U.S. PATENT DOCUMENTS 5,867,210 A * 2/1999 Rod .................... H04N 13/341
348/E13.043
6,471,363 B2 * 10/2002 Howell .................. F16M 11/24
362/11
10,799,314 B2 * 10/2020 Beaumont ............. A61B 90/35
(Continued)

FOREIGN PATENT DOCUMENTS

CN 109893257 A 6/2019
CN 109893258 A 6/2019
(Continued)

*Primary Examiner* — Alexander K Garlen
(74) *Attorney, Agent, or Firm* — Troutman Pepper Locke LLP

(57) ABSTRACT

A medical imaging device according to the present invention includes an illumination unit that spot-illuminates a center of operative field of a surgical patient, an operative field camera unit that images a center of irradiation range by the illumination unit, a housing that covers the illumination unit and the operative field camera unit, and a pair of display units and that are visible from both sides of the surgical patient.

16 Claims, 12 Drawing Sheets

(56) References Cited

U.S. PATENT DOCUMENTS

| | | | | |
|---|---|---|---|---|
| 11,253,334 | B2 * | 2/2022 | Mueller | A61B 90/20 |
| 11,389,265 | B2 * | 7/2022 | Steffen | H04N 23/57 |
| 12,207,977 | B2 * | 1/2025 | Allen | A61B 90/50 |
| 2015/0327765 | A1 * | 11/2015 | Crane | A61B 5/489 348/77 |
| 2016/0128553 | A1 | 5/2016 | Geng | |
| 2017/0143442 | A1 * | 5/2017 | Tesar | H04N 23/63 |
| 2018/0263723 | A1 * | 9/2018 | Beaumont | H04N 23/50 |
| 2019/0076006 | A1 | 3/2019 | Takeda | |
| 2020/0008899 | A1 * | 1/2020 | Tripathi | H04N 13/15 |
| 2021/0011272 | A1 * | 1/2021 | Ko | G02B 27/0025 |
| 2021/0244479 | A1 | 8/2021 | Wassall et al. | |
| 2023/0120611 | A1 * | 4/2023 | Polchin | A61B 90/25 348/47 |

FOREIGN PATENT DOCUMENTS

| | | | | | |
|---|---|---|---|---|---|
| CN | 110192390 | A | * | 8/2019 | H04N 13/344 |
| CN | 210727882 | U | | 6/2020 | |
| CN | 210902962 | U | | 7/2020 | |
| CN | 214405511 | U | | 10/2021 | |
| CN | 114466124 | A | * | 5/2022 | H04N 23/51 |
| JP | 2004-113805 | A | | 4/2004 | |
| JP | 2004-337442 | A | | 12/2004 | |
| JP | 2006-061702 | A | | 3/2006 | |
| JP | 2019-42413 | A | | 3/2019 | |
| JP | 2021-126519 | A | | 9/2021 | |
| WO | WO-2019210322 | A1 | * | 10/2019 | A61B 90/361 |

* cited by examiner

MEDICAL IMAGING DEVICE

TECHNICAL FIELD

The present invention relates to a medical imaging device that images a center of operative field of a surgical patient.

BACKGROUND ART

It is an essential function of current operating room to clearly take a video of a center of operative field of surgical operation and display it in the operating room or record the video. For example, it is possible to contribute to improvement of safety of surgery by providing operative field information to a second assistant standing at a position where the operative field cannot be directly visually recognized or a medical assistant who provides medical instruments, and it is also useful for learning of medical students, nursing students, and the like in the operating room to observe the state of surgery. On the other hand, recording image information that clearly captures the whole of surgery is an important medical record from the viewpoint of medical safety, and is also important as a review learning and conference presentation material for surgeons. However, in a body surface surgery or an open surgery such as a laparotomy, which occupies most of surgical operation, many operative field videos are shielded by a head or a body of an operator, and there are many cases where a center of operative field is not sufficiently captured.

Currently, shooting and recording of operative field in the open surgery such as the body surface surgery or the laparotomy are performed by an operative field camera incorporated in a center of a surgical light disposed above a surgeon's head or an operative field camera mounted on another arm. In order to appropriately image the center of operative field of the patient, it is necessary for the surgeon to temporarily stop the surgical operation and adjust the position of the operative field camera while directing his/her line of sight to a display device provided on a wall surface or the like in the operating room. Alternatively, the operator who concentrates on surgical procedure is not conscious of the recording of the operative field, and as a result, a useless video that is not appropriately aligned to the operative field is often vaguely projected and recorded.

In such a situation in a medical site, in order to reliably obtain an appropriate image of the center of operative field, it is necessary to arrange a dedicated videographer other than the surgeon who performs a surgery and frequently adjust the position of imaging device, and the surgery video is recorded in such a manner at the time of special and valuable surgery. On the other hand, in a medical site having chronic shortage of personnel, facilities in which such personnel can be arranged for all surgeries are limited, and there has been no method for simply and reliably obtaining the surgery video contributing to medical safety, education, and academia without arranging the dedicated videographer.

In recent years, an attempt has been made to shoot an operative field video with a small camera attached to the head of an operator, a frame of glasses, or the like by applying a miniaturized imaging device. An advantage of such an imaging device is that the imaging device is not shielded at all by the head, the shoulder, or the like of the operator, but since the image is blurred with the movement of the head of the operator, it is not possible to shoot a video that can withstand observation, and such imaging device is not accepted in the actual clinical site, and is not widely used.

On the other hand, clear illumination of operative field is essential for surgery, and in most operating rooms around the world, it is carried by a surgical light composed of multiple light sources placed above the surgeon's head. However, in many cases, the light is blocked by the head or the body of the operator and the illumination becomes insufficient, and the surgeon frequently adjusts position of the illumination device so that the center of the illumination coincides with the center of the operation target by holding a sterile handle by himself/herself.

As a measure to compensate for insufficient illumination by the surgical light disposed above the head, it is very effective to illuminate a center of operative field supplementally with a spotlight device attached to the forehead of the operator, and many surgeons use it on a daily basis. The area of the light field illuminating the center of operative field varies from about 3 cm to 15 cm in diameter depending on the type of surgery, but the surgeon prepares and uses the spotlight device having the light field suitable for each surgery. Since adjusting the position of the spotlight that illuminates the center of operative field improves the workability of the surgery, the surgeon does not spare effort for the action. Although the light field of the spotlight slightly moves due to the movement of the operator's head, the movement is not uncomfortable for the surgeon himself or the assistant such as the second assistant, and does not hinder the surgery. Above all, it is also a great advantage that medical assistants or learners can know that the place illuminated by the surgeon with the spotlight is the center of operative field.

Patent Literature 1 discloses a medical observation apparatus in which an imaging device is attached to a distal end of an arm in a magnifying glass surgery performed by a surgeon looking into a microscope instead of an open surgery which is an object of the present invention. The imaging device images a subject such as an operative site of a patient. The captured medical image is displayed on a display device provided separately from the medical observation apparatus.

CITATION LIST

Patent Literature

Patent Literature 1: JP 2019-42413 A

SUMMARY OF INVENTION

Technical Problem

However, the medical observation apparatus disclosed in Patent Literature 1 is a microscopic surgery apparatus, and an operator basically performs surgery while viewing image information captured by this apparatus. In addition, the main purpose of the medical observation apparatus disclosed in Patent Literature 1 is to acquire images using light sources having different wavelengths, and the medical observation apparatus does not contribute to an illumination function in an open surgery such as a body surface surgery or a laparotomy, and the device according to the present invention for capturing an operative field image.

In view of the above problems, it is an object of the present invention to provide a medical imaging device capable of continuing to clearly image the center of operative field of a surgical patient in the open surgery such as the body surface surgery or the laparotomy without interruption of the surgery by the operator for the purpose of imaging or without assistance of a third imaging assistant.

Solution to Problem

A medical imaging device according to the present invention made to solve the above problems includes: an illumination unit configured to spot-illuminate a center of operative field of a surgical patient; an operative field camera unit configured to capture an image of a center of irradiation range by the illumination unit; a housing that covers the illumination unit and the operative field camera unit; and a pair of display units visually recognizable from both sides of the surgical patient.

With this configuration, as long as the operator performs the surgery by adjusting the irradiation range of the illumination unit to the center of operative field, it is possible to continue to appropriately image the clear center of operative field of the surgical patient without separately interrupting the surgery for the purpose of imaging and without obtaining the assistance of the third imaging assistant.

In addition, in the medical imaging device of the present invention, the illumination unit includes a plurality of light sources, the plurality of light sources is arranged on a diagonal line or in a ring shape so as to surround a periphery of the operative field camera unit with the operative field camera unit as a center, and the illumination unit is provided at an angle at which an illumination optical axis of the illumination unit and an image axis of the operative field camera unit coincides with each other on the center of operative field.

With this configuration, the illumination unit can appropriately illuminate the center of operative field of the surgical patient, and the operative field camera unit can accurately image the center of operative field irradiated by the illumination unit.

In addition, the medical imaging device according to the present invention includes a reflection unit that reflects irradiation light emitted from the illumination unit to coincide with an image axis of the operative field camera unit.

With this configuration, the illumination unit can appropriately illuminate the center of operative field of the surgical patient, and the operative field camera unit can accurately image the center of operative field irradiated by the illumination unit.

In addition, in the medical imaging device of the present invention, the illumination unit and the operative field camera unit are arranged in parallel, and the illumination unit is installed at an angle at which an illumination optical axis of the illumination unit coincides with the image axis of the operative field camera unit arranged on the center of operative field.

With this configuration, the illumination unit can appropriately illuminate the center of operative field of the surgical patient, and the operative field camera unit can accurately image the center of operative field irradiated by the illumination unit.

In addition, the medical imaging device according to the present invention includes an adjusting unit that adjusts a direction of an image displayed on the display unit.

With this configuration, the direction of the image displayed on the display unit can be matched with the visual field actually viewed directly.

In addition, a medical imaging device according to the present invention includes an inclination adjusting unit that adjusts an angle formed by the illumination optical axis of the illumination unit and an image axis of the operative field camera unit, and the inclination adjusting unit adjusts the angle formed.

With this configuration, the operative site camera unit can appropriately image the center of operative field irradiated by the illumination unit.

In addition, in the medical imaging device of the present invention, the pair of display units is provided on both side surfaces of the housing.

With this configuration, the entire configuration can be made compact.

In addition, in the medical imaging device of the present invention, the illumination unit spot-illuminates the center of operative field of the surgical patient from a position of 10 cm to 150 cm away from the operative field.

Advantageous Effects of Invention

In a medical imaging device of the present invention, an illumination optical axis of an illumination unit and an image axis of an operative field camera unit can be easily made to coincide with each other, and even when an imaging assistant is absent, an operative site of a patient can be appropriately imaged when an operator performs a surgery by adjusting the illumination optical axis of the illumination unit to a center of operative field.

BRIEF DESCRIPTION OF DRAWINGS

FIG. 9 is a block diagram of the first example of the medical imaging device according to the embodiment of the present invention.

BEST MODE FOR CARRYING OUT THE INVENTION

Figure 1:
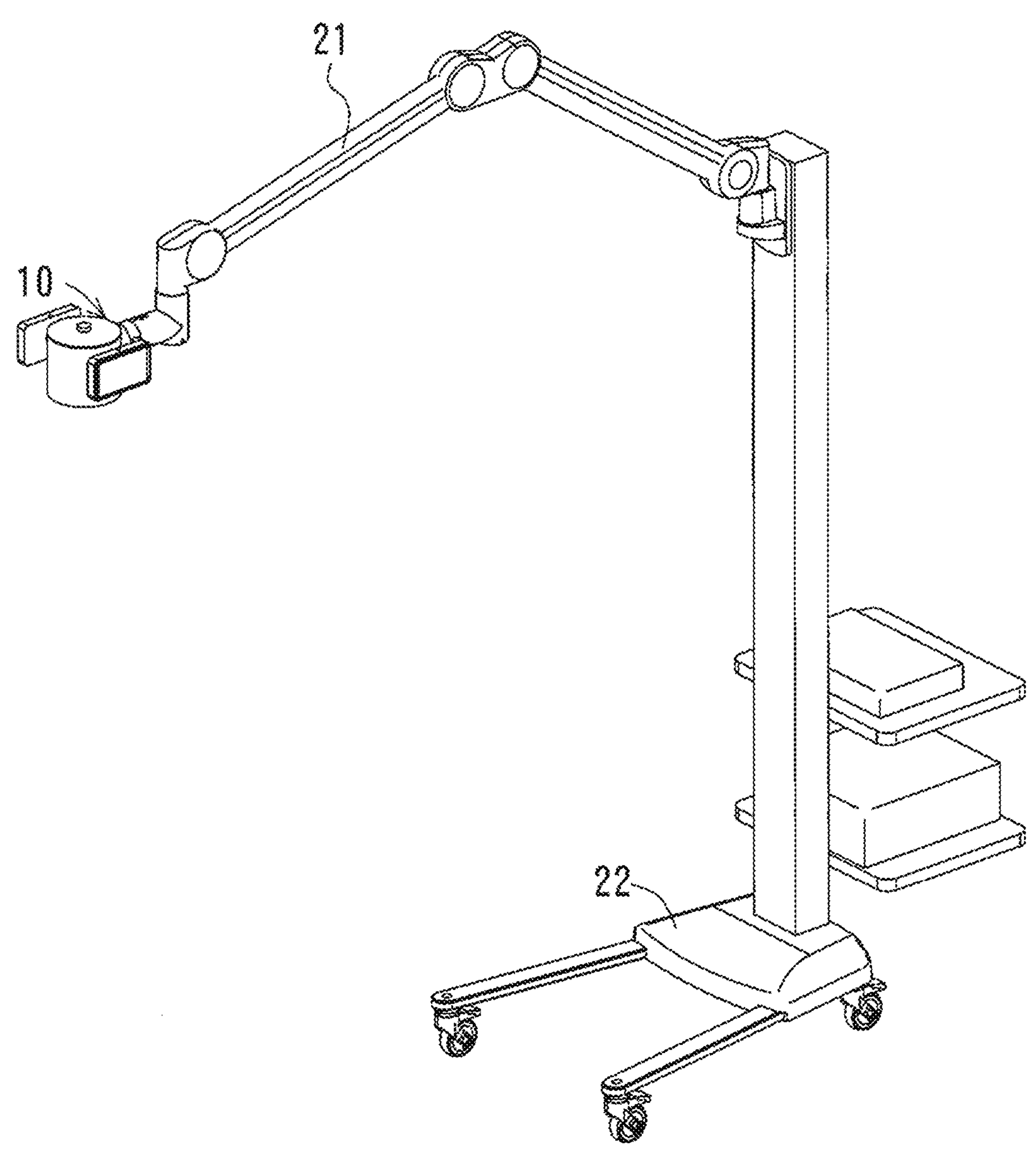
FIG. 1 is an overall schematic view of a medical imaging device according to an embodiment of the present invention.
Figure 2:
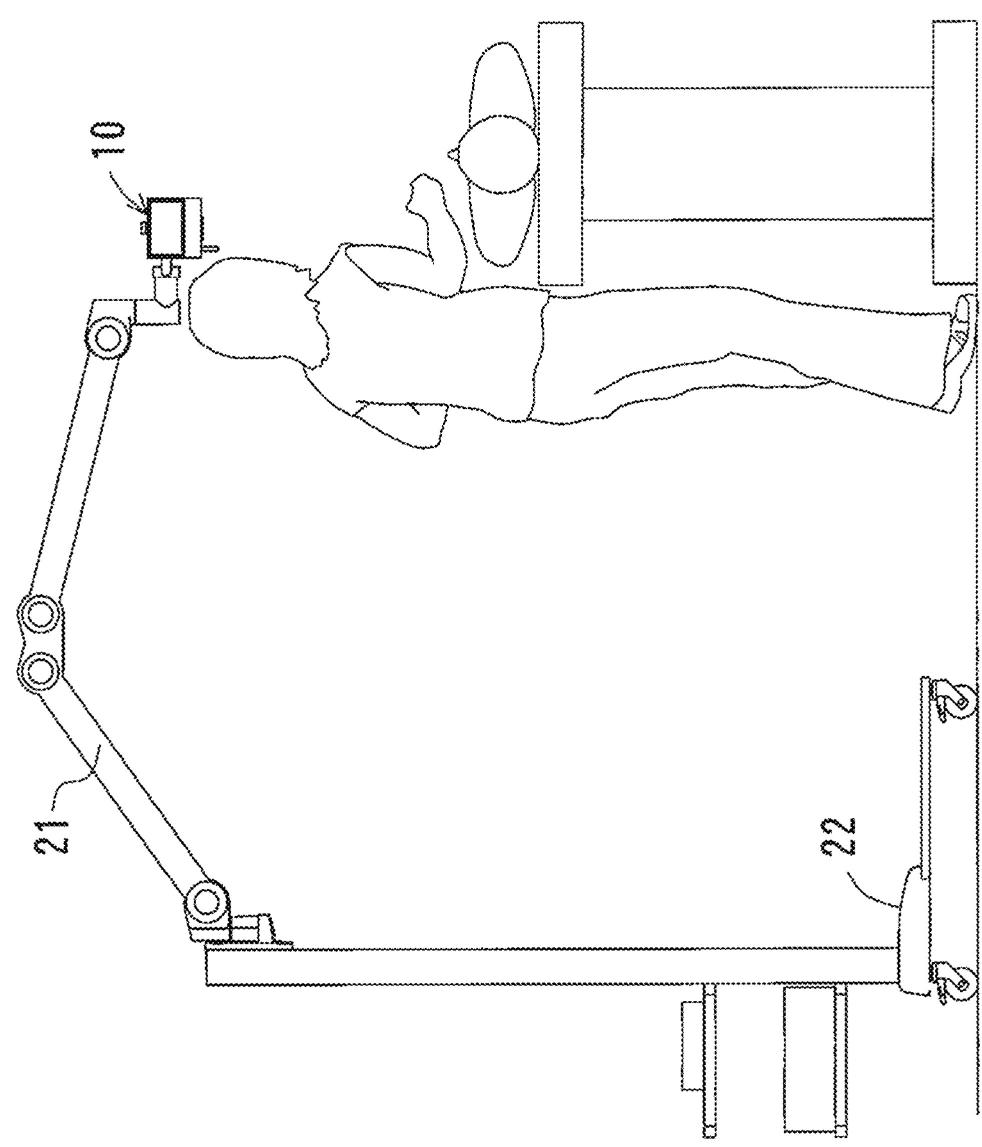
FIG. 2 is an explanatory view illustrating a state in which the medical imaging device according to the embodiment of the present invention is used.

Hereinafter, a medical imaging device according to an embodiment of the present invention will be described with reference to the accompanying drawings. FIG. 1 is an overall schematic view of a medical imaging device according to an embodiment of the present invention. Furthermore, FIG. 2 is an explanatory diagram illustrating a state in which the medical imaging device according to the embodiment of the present invention is used.

The medical imaging device 10 of the present embodiment is attached to the distal end of an arm unit 21 in which a plurality of joint portions is connected via a plurality of link units. Since the arm unit 21 is configured to be rotatable about rotation axis of the joint portion and can be easily linearly extended or folded at a position not hindering surgery by an operator, the medical imaging device 10 of this embodiment can be disposed at a position of 10 cm to 150 cm away from the operative field. Note that the arm unit 21 may be provided with a brake portion that restricts rotation at the joint portion.

Furthermore, the medical imaging device 10 of the present embodiment may be attached to a base portion 22 provided with a caster and freely movable on a floor surface of the operating room. As illustrated in FIG. 2, the medical imaging device 10 of the present embodiment can be moved in the operating room by the base portion 22 in accordance with a surgical site of a patient.

Figure 3:
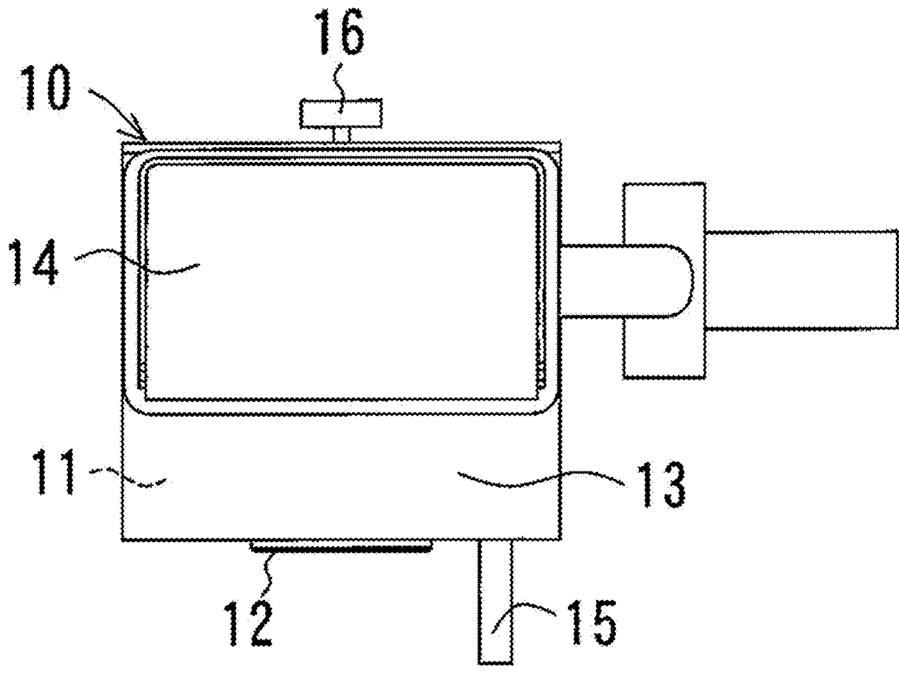
FIG. 3 is a side view illustrating a first example of the medical imaging device according to the embodiment of the present invention.
Figure 4:
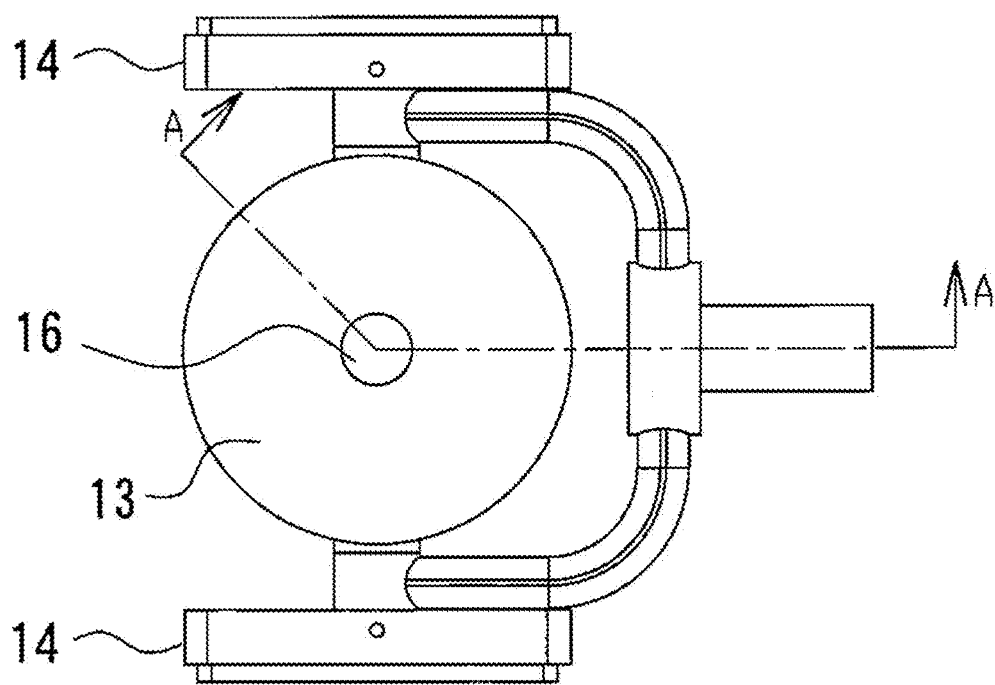
FIG. 4 is a plan view of the first example of the medical imaging device according to the embodiment of the present invention.
Figure 5:
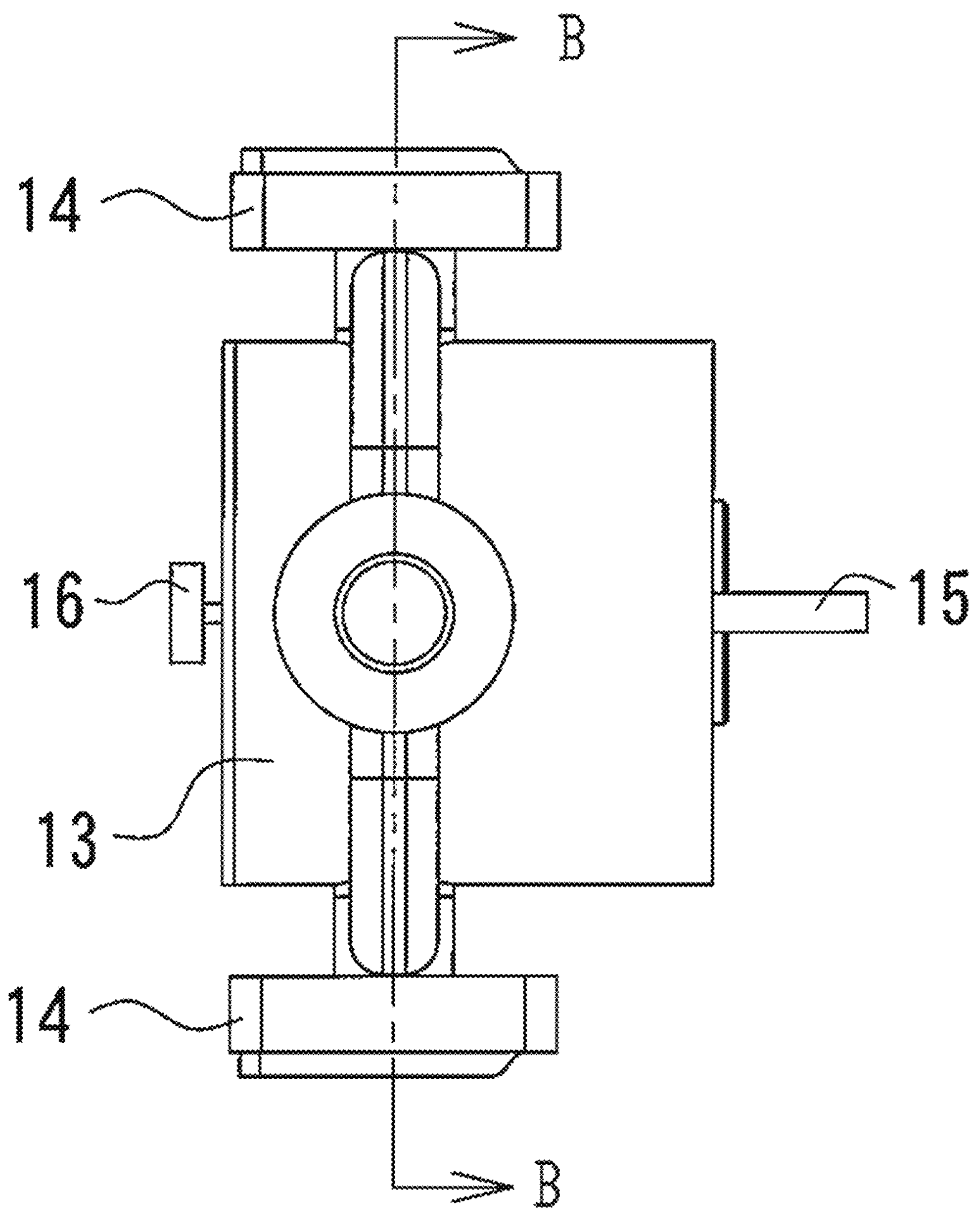
FIG. 5 is a rear view of the first example of the medical imaging device according to the embodiment of the present invention.
Figure 6A:
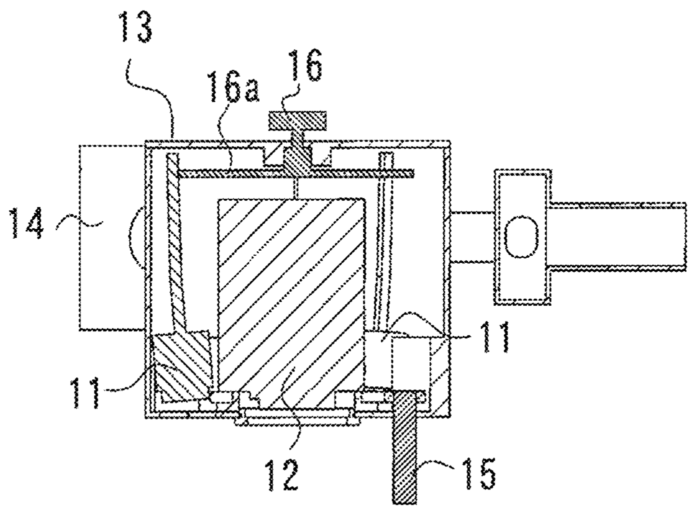
FIG. 6(*a*) is a cross-sectional view taken along line A-A illustrated in FIG. 4, and FIG. 6(*b*) is a cross-sectional view taken along line B-B illustrated in FIG. 5.
Figure 6B:
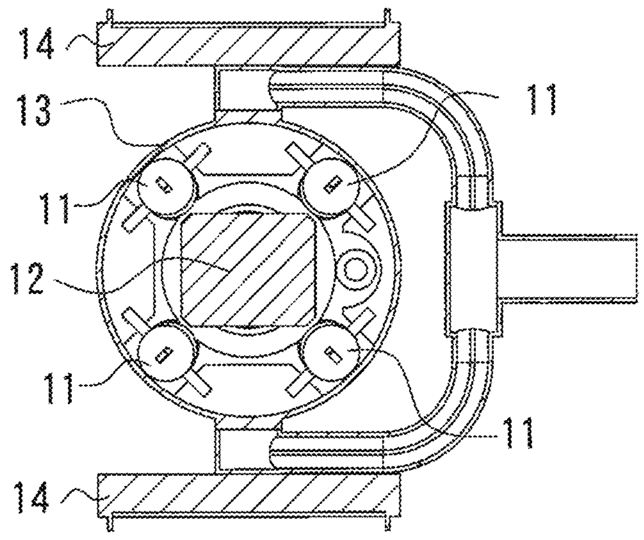

First, a first example of the medical imaging device 10 of the present embodiment will be described below. FIG. 3 is a side view illustrating the first example of the medical imaging device according to the embodiment of the present invention. FIG. 4 is a plan view of the first example of the medical imaging device according to the embodiment of the present invention. Furthermore, FIG. 5 is a rear view of the first example of the medical imaging device according to the embodiment of the present invention. FIG. 6(*a*) is a cross-sectional view taken along line A-A illustrated in FIG. 4, and FIG. 6(*b*) is a cross-sectional view taken along line B-B illustrated in FIG. 5.

The medical imaging device 10 according to the first example includes an illumination unit 11 that spot-illuminates an operative field center C of a surgical patient, an operative field camera unit 12 that images the operative field center C of the surgical patient, the illumination unit 11, and a pair of display units 14 and 14 visible from both sides of the surgical patient. Note that the illumination unit 11 of the medical imaging device 10 according to the first example can be arranged at a position 10 cm to 150 cm away from the operative field, that is, at a position not disturbing the operator, and can spot-illuminate the center of operative field of the surgical patient.

Figure 7:
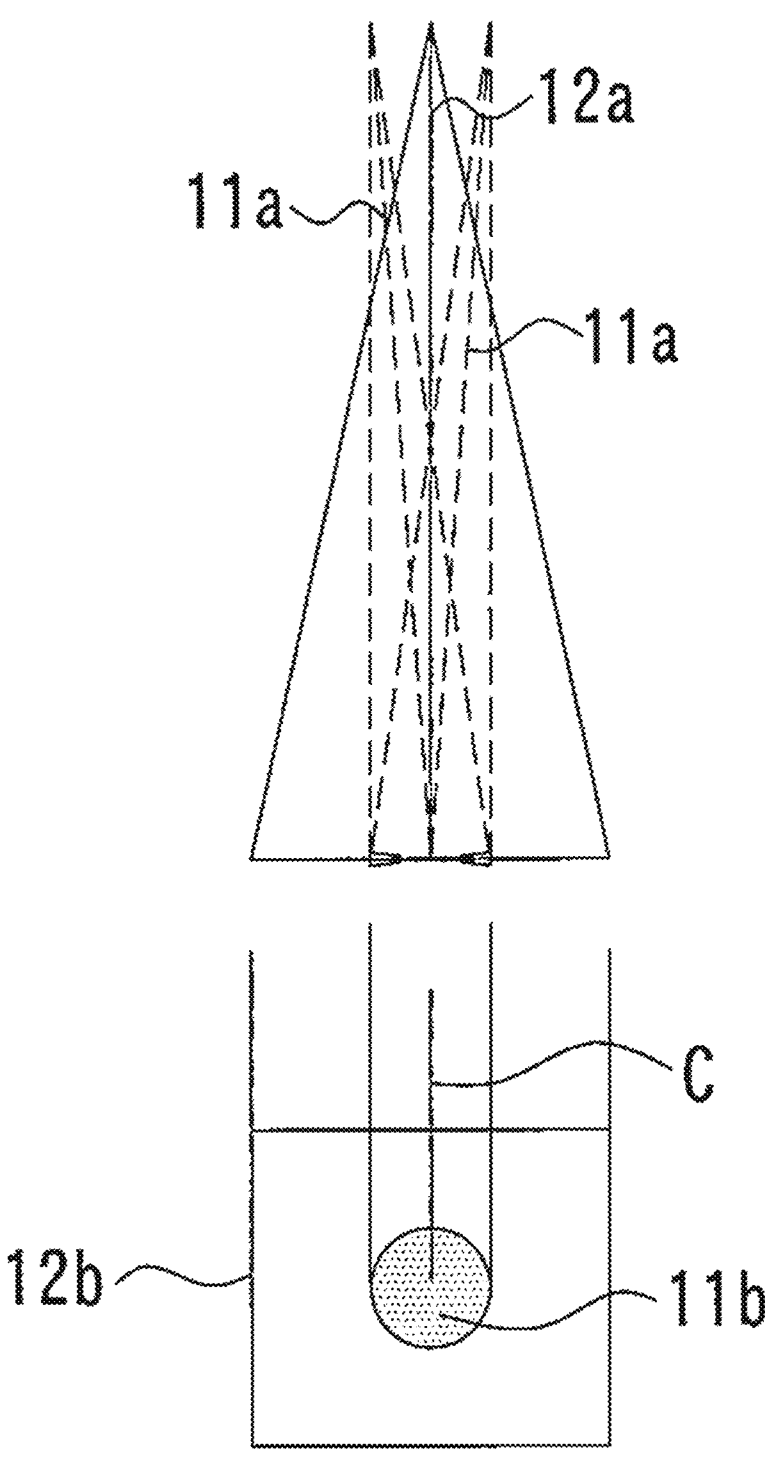
FIG. 7 is an explanatory view illustrating a state in which an illumination optical axis of an illumination unit and an image axis of an operative field camera unit coincide with each other according to the medical imaging device of the embodiment of the present invention.

As illustrated in FIGS. 6(*a*) and 6(*b*), the illumination unit 11 includes a plurality of light sources, that is, two or more light sources. The plurality of light sources is arranged so as to surround the operative field camera unit 12 with the operative field camera unit 12 as the center. As illustrated in FIG. 7, the illumination unit 11 is provided at an angle at which an illumination optical axis 11*a* of the illumination unit 11 coincides with an image axis 12*a* of the operative field camera unit 12 arranged on the operative field center C.

Here, since the illumination optical axis 11*a* of the illumination unit 11 is provided at an angle at which the illumination optical axis 11*a* coincides with the image axis 12*a* of the operative field camera unit 12 arranged on the operative field center C, a light field 11*b* of the illumination unit 11 is positioned at the operative field center C, the light field size thereof is set to φ3 cm or more and 15 cm or less, and the center of operative field can be appropriately irradiated. Note that the reference numeral 12*b* in FIG. 7 indicates the angle of view of the operative field camera unit 12.

In addition, the illumination unit 11 includes a plurality of light sources, is arranged on a diagonal line, and preferably has illuminance that is not canceled even under high illuminance under a surgical light and can determine the outline of the operative site. The illuminance of the center of operative field obtained by combining the illuminance of the surgical light and the illuminance of the illumination unit 11 is preferably 50,000 1× or more, more preferably 80,000 1× or more, and particularly preferably 100,000 1× or more.

Furthermore, in a case where the illumination unit 11 is disposed at a position of 10 cm to 150 cm away from the operative field, it is preferable to include a light field adjustment unit (not illustrated) capable of adjusting the light field size within a range of 3 cm to 15 cm in diameter.

The operative field camera unit 12 captures an image of a subject such as an operative site of a patient, for example, and transmits captured image data of the operative site of the patient or the like to a storage unit 32 described later.

Furthermore, since the operative field camera unit 12 does not require a plurality of cameras and is a single camera, the size of the operative field camera unit 12 can be reduced. Therefore, even if the operative field camera unit 12 is arranged close to an operator of a patient and in the center of operative field of the patient, the operative field camera unit does not come into contact with the head or the shoulder of the operator, and does not interfere with the surgery by the operator. Specifically, the operative field camera unit 12 is provided with a camera member in a cylindrical member in which an opening is formed at a lower end. Further, a cover glass for protecting the camera member is provided at an end portion of the camera member. Here, the camera member includes an optical system and an image sensor including an imaging element that captures an image of an imaging target, for example, an operative site of a patient by light passing through the optical system. Here, the optical system includes lenses such as an objective lens, a zoom lens, and a focus lens, and the image sensor is an image sensor including a plurality of imaging elements such as CMOS and CCD.

A housing 13 houses the illumination unit 11 and the operative field camera unit 12, and the display units 14 and 14 are attached to both side surfaces thereof. In addition, it is preferable that the housing 13 does not hinder an operation by an operator and is formed with a size as small as possible.

The display units 14 and 14 are provided, for example, on both side surfaces of the housing 13 so as to be visible from both sides of the surgical patient, and the operative site of the patient imaged by the operative field camera unit 12 is displayed. In addition, since the display units 14 and 14 can be arranged in front of the eyes of the operator, it is not necessary for the operator to move the head or the eye line largely in order to see the operative site displayed on the display units 14 and 14 at the time of surgery. In this manner, even if the operator performs surgery standing on either the left or the right of the patient, the operator can easily confirm the operative site by the display units 14 and 14. Furthermore, it is preferable that the display units 14 and 14 include, for example, a liquid crystal display, an organic EL display, or the like, and have dimensions that do not interfere with surgery by the operator. Note that the display units 14 and 14 are driven by power supplied from a drive unit 34 described later or power supplied from a connected external power supply.

Furthermore, the medical imaging device 10 according to the first example preferably includes an adjusting unit 15 that adjusts the direction of the image displayed on the display units 14 and 14. When the adjusting unit 15 is operated, that is, rotated by the operator, the operative field camera unit 12 is rotated via a rotation gear (not illustrated), and the orientation of the image displayed on the display units 14 and 14 can be adjusted so as to match the visual field directly viewed by the operator.

Here, the operator can arrange the medical imaging device 10 according to the first example at a position suitable for imaging the operative field, that is, at a position of 10 cm to 150 cm away from the operative field while holding the adjusting unit 15.

Furthermore, since the adjusting unit is touched by the operator's hand, the surface of the adjusting unit 15 is preferably covered with sterilizing/virus-destroying resin. In addition, it is preferable that the adjusting unit 15 can be repeatedly used because sterilization and virus-killing effect are exerted by performing sterilization treatment again. Furthermore, the adjusting unit 15 may be formed of a material having a large friction coefficient so that the operator does not slip his/her hand when performing an operation, and an uneven shape may be formed on the surface thereof.

Furthermore, the medical imaging device 10 according to the first example preferably includes an inclination adjusting unit 16 that adjusts the angle θ formed by the illumination optical axis 11*a* of the illumination unit 11 and the image axis 12*a* of the operative field camera unit 12. The inclination adjusting unit 16 can adjust the inclination of the illumination unit 11 via a connecting member 16*a* connected to the illumination unit 11, and can adjust the angle formed by the illumination optical axis 11*a* of the illumination unit 11 and the image axis 12*a* of the operative field camera unit 12 in a range of, for example, 2° or more and 4° or less.

Figure 8B:
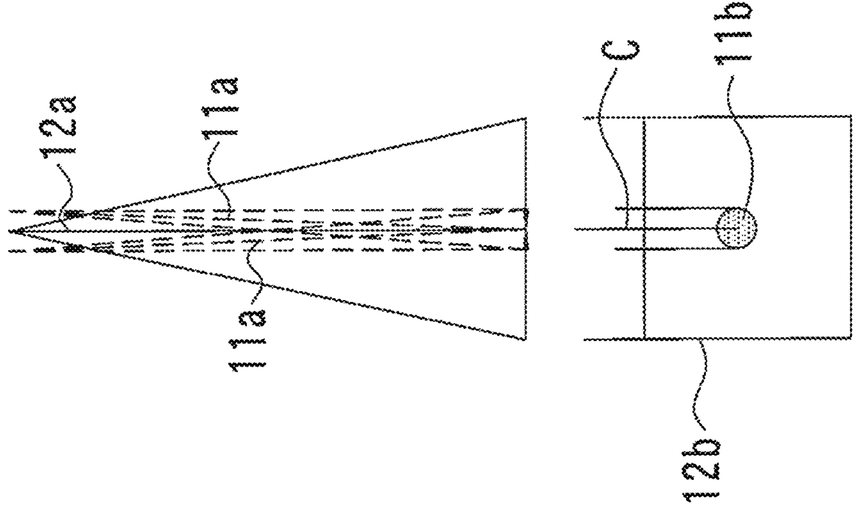
FIG. 8(*a*) is an explanatory diagram illustrating a state in which an illumination optical axis of an illumination unit and an image axis of an operative field camera unit according to the medical imaging device according to the embodiment of the present invention do not coincide with each other, and FIG. 8(*b*) is an explanatory diagram illustrating a state in which the illumination optical axis of the illumination unit and the image axis of the operative field camera unit coincide with each other.
Figure 8A:
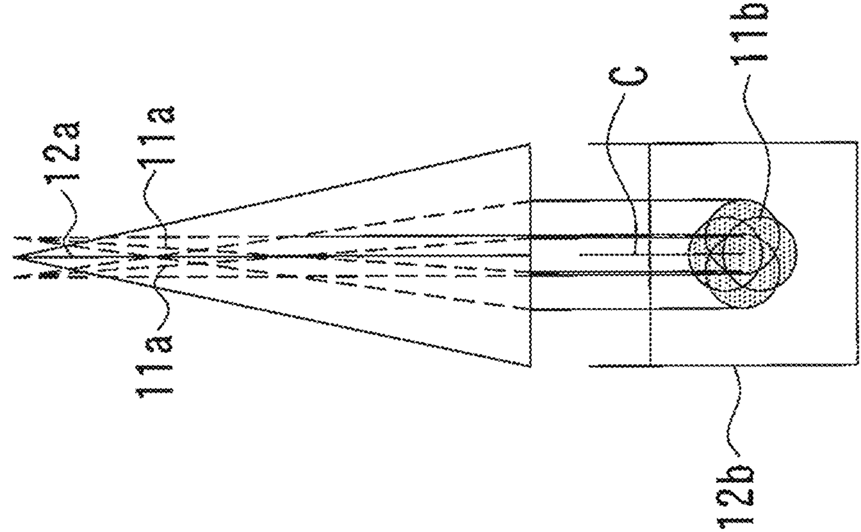

Specifically, as illustrated in FIG. 8(*a*), in a case where the illumination optical axis 11*a* of the illumination unit 11 does not coincide with the image axis 12*a* of the operative field camera unit 12 arranged on the operative field center C, there is a case where the light field 11*b* formed by the plurality of light sources of the illumination unit 11 is blurred and the range of the light field 11*b* is difficult to recognize. Therefore, when the operator operates the inclination adjusting unit 16 to adjust the angle between the illumination optical axis 11*a* of the illumination unit 11 and the image axis 12*a* of the operative field camera unit 12, as illustrated in FIG. 8(*b*), the light field 11*b* on the operative field formed by the illumination unit 11 becomes clear, and thus the operator can easily adjust the position of the light field 11*b* to the portion where the illumination optical axis 11*a* coincides with the operative field center C. On the other hand, the image axis 12*a* always coincides with the center of light field 11*b* regardless of whether the light field 11*b* is slightly blurred as illustrated in FIG. 8(*a*) or clear as illustrated in FIG. 8(*b*), and thus, it is possible to appropriately capture the center of operative field of the patient. In this manner, the illumination unit 11 and the operative field camera unit 12 can be synchronized with each other.

Note that the medical imaging device 10 according to the first example may include a mechanism that adjusts the diameter of the light field 11*b* of the illumination unit 11 according to zoom and pan of the operative field camera unit 12, that is, the angle of view 12*b*. With this mechanism, even when the angle of view 12*b* changes, a suitable light field 11*b* can be obtained. Furthermore, the medical imaging device 10 according to the first example includes an automatic focus adjustment mechanism, that is, a mechanism that adjusts the illumination optical axis 11*a* and the diameters of the light field 11*b* of the illumination unit 11 according to the focal position. With this mechanism, even when the operator changes the distance to the operative site, an irradiation light axis 11*a* and the light field 11*b* can be adjusted to be suitable. In addition, even in a case where there is a plurality of light sources like the illumination unit 11, it is preferable to include a mechanism that adjusts the illumination optical axis 11*a* and the light field 11*b* of each of the plurality of light sources in conjunction with each other between the light sources according to the focal position.

Figure 9:
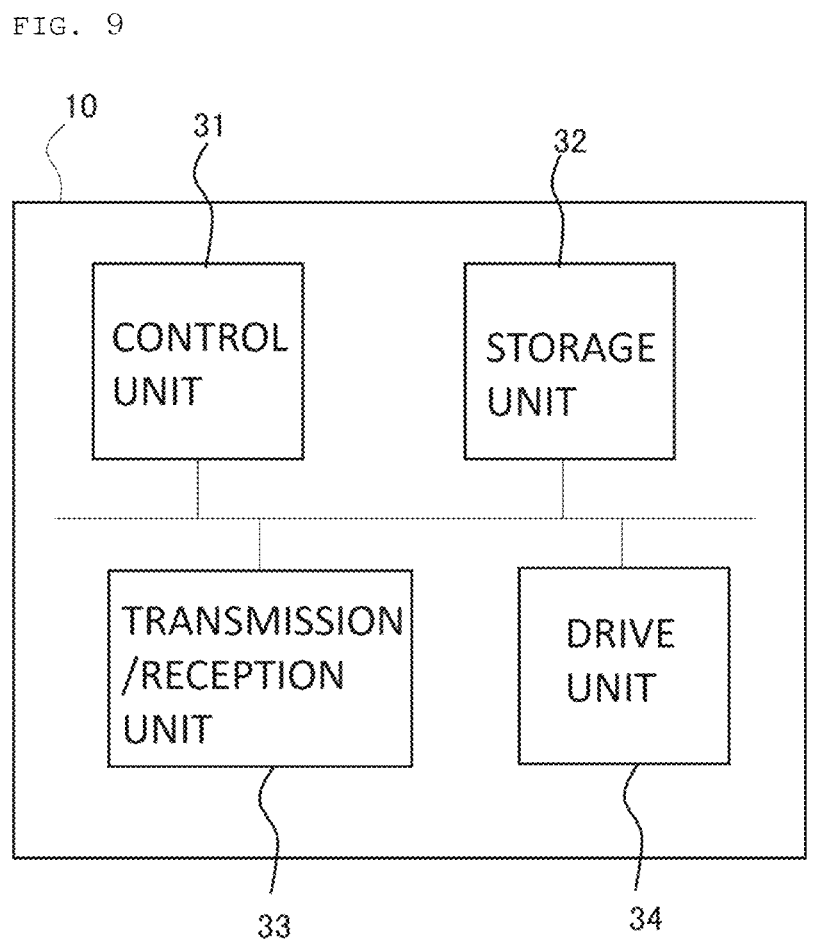

Furthermore, as illustrated in FIG. 9, the medical imaging device 10 according to the first example includes a control unit 31, the storage unit 32, and a transmission/reception unit 33 inside the housing 13.

The control unit 31 includes CPU or the like, and controls the illumination unit 11, the operative field camera unit 12, and the like.

The storage unit 32 stores imaging data of an operative site of a patient imaged by the operative field camera unit 12. Furthermore, the storage unit 32 stores programs for controlling the illumination unit 11, the operative field camera unit 12, and the like, calculation parameters, execution programs, various data, and the like. Specifically, examples of the storage unit 42 include a magnetic recording medium such as a hard disk, a nonvolatile memory such as a flash memory, and the like. Note that the storage unit 32 may be provided inside the housing 13, or may be provided in an external device (not illustrated) of the medical imaging device 10 according to the first example by the transmission/reception unit 33 to be described later.

The transmission/reception unit 33 can transmit and receive various data and the like to and from an external device in a wireless or wired manner.

Furthermore, the medical imaging device 10 according to the first example may include the drive unit 34 such as a battery inside the housing 13. The drive unit 34 may not be built in the housing 13 but may be electrically connected to an external power supply.

Figure 10:
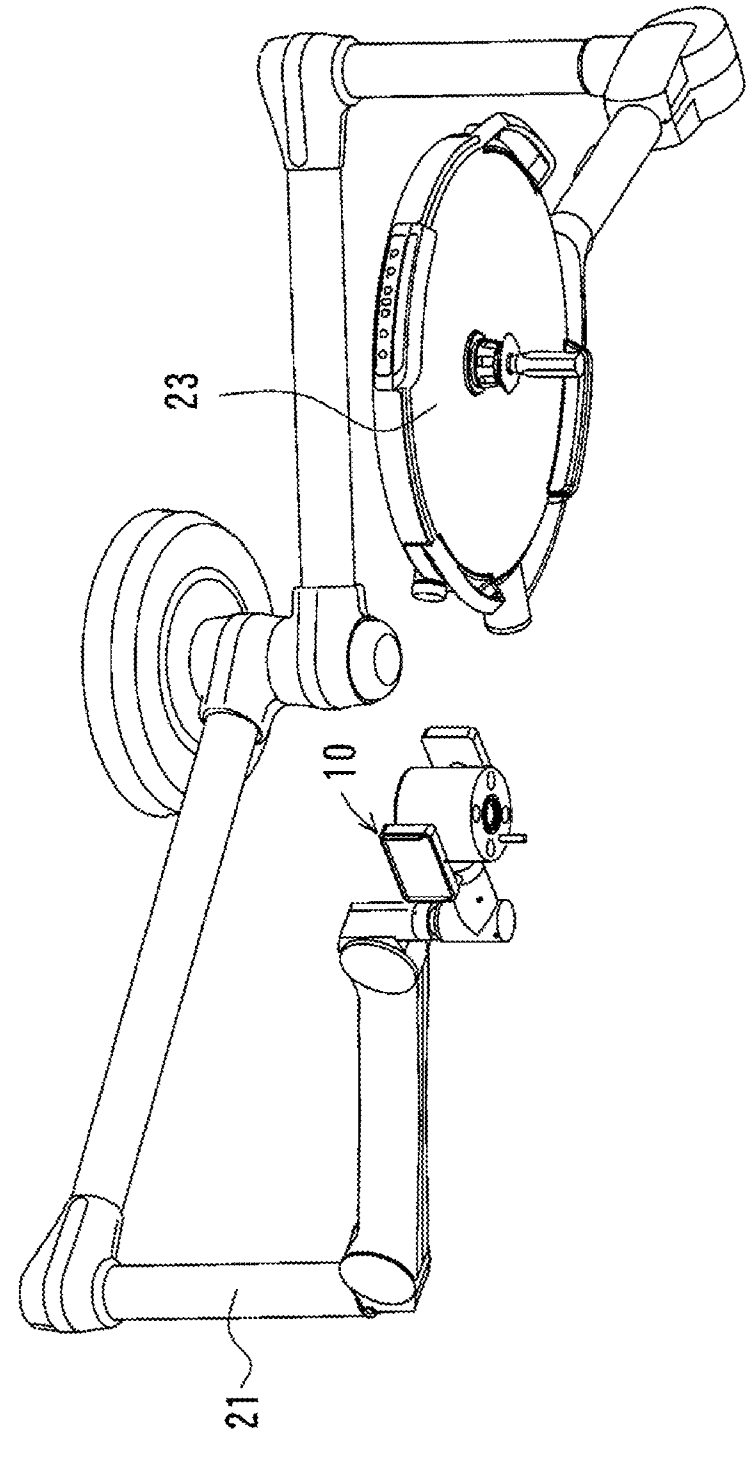
FIG. 10 is an explanatory diagram illustrating a modification of the first example of the medical imaging device according to the embodiment of the present invention.

Furthermore, as illustrated in FIG. 10, the medical imaging device 10 according to the first example may be configured to be attached to a surgical light 23 attached to the ceiling of the operating room. The medical imaging device 10 according to the first example is configured to be suspended from the surgical light 23, and is less likely to be an obstacle when an operator performs a surgery.

Figure 11:
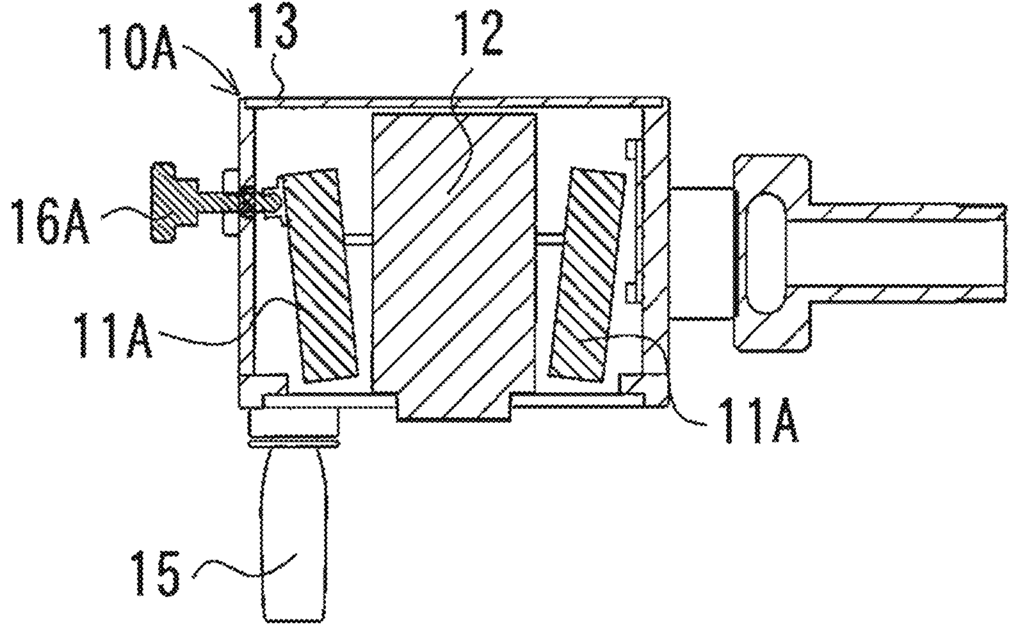
FIG. 11 is an explanatory diagram illustrating a second example of the medical imaging device according to the embodiment of the present invention.

A second example of the medical imaging device 10 of the present embodiment is as illustrated in FIG. 11, and a configuration different from that of the first example will be described below. Note that components similar to those of the medical imaging device 10 according to the first example are denoted by the same reference numerals, and description thereof will be omitted.

A medical imaging device 10A according to the second example includes an inclination adjustment unit 16A capable of adjusting the inclination of an illumination unit 11A.

The inclination adjustment unit 16A can adjust the inclination of the illumination unit 11A by pressing the illumination unit 11A, and can adjust the inclination in an angle formed by an illumination optical axis 11*a* of the illumination unit 11A and an image axis 12*a* of an operative field camera unit 12A, for example, in a range of 3° or more and 6° or less.

Figure 12:
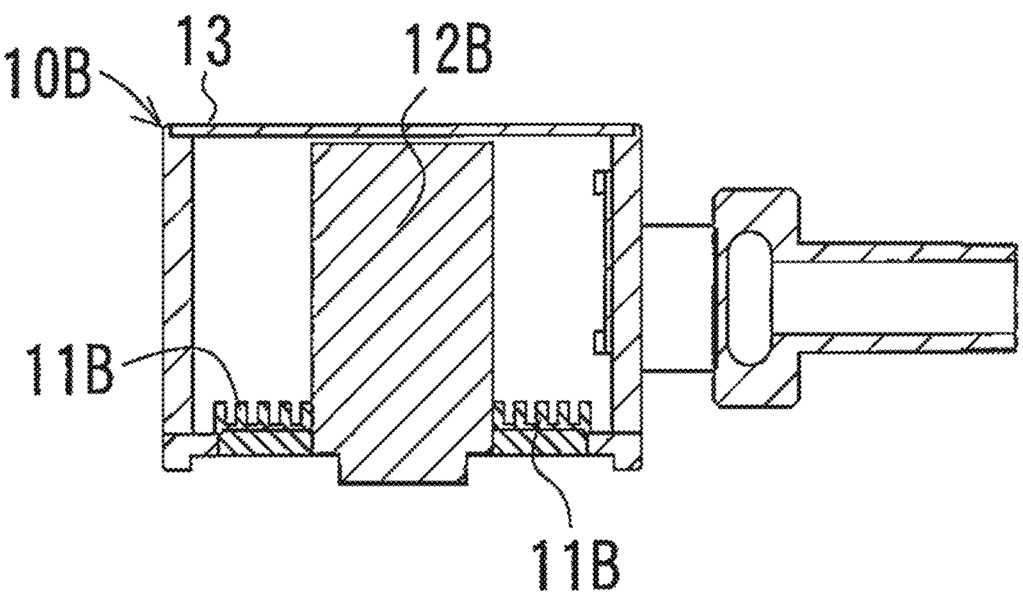
FIG. 12 is an explanatory diagram illustrating a third example of the medical imaging device according to the embodiment of the present invention.

A third example of the medical imaging device 10 of the present embodiment is as illustrated in FIG. 12, and configurations different from those of the first and second examples will be described below. Note that components similar to those of the medical imaging device 10 according to the first example are denoted by the same reference numerals, and description thereof will be omitted.

A medical imaging device 10B according to the third example includes an illumination unit 11B including a plurality of light sources and arranged in a ring shape so as to surround the periphery of the operative field camera unit 12.

The illumination unit 11B is arranged in a ring shape so as to surround the periphery of the operative field camera unit 12B, and is provided to be inclined at an angle at which an illumination optical axis 11*a* of the illumination unit 11B coincides with an image axis 12*a* of the operative field camera unit 12B arranged on the operative field center C.

Figure 13:
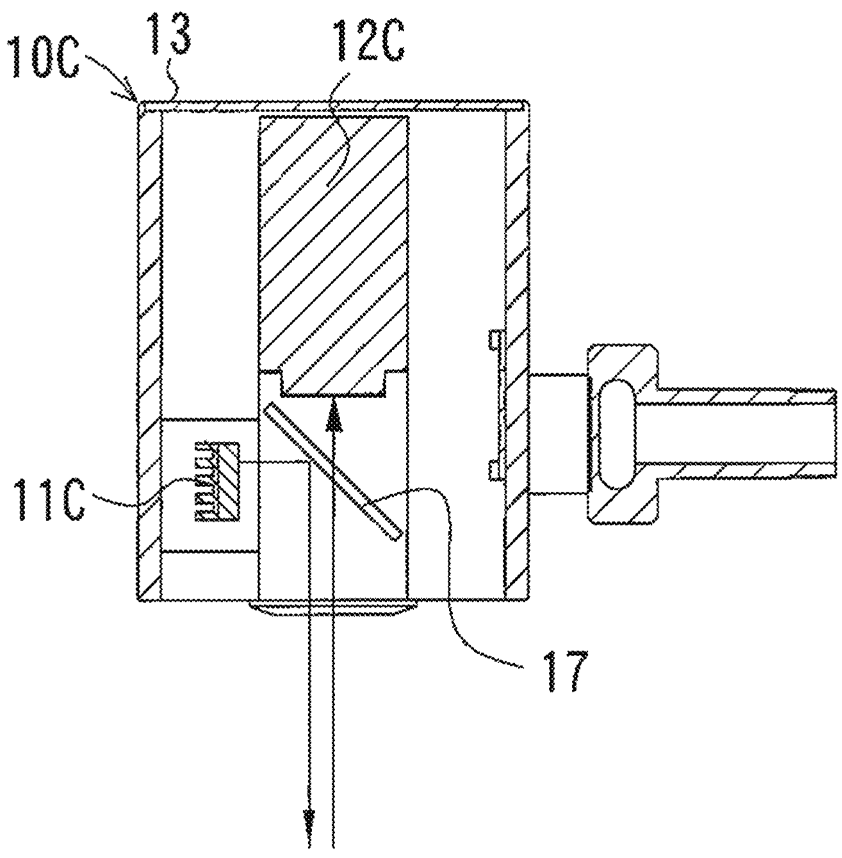
FIG. 13 is an explanatory diagram illustrating a fourth example of the medical imaging device according to the embodiment of the present invention.

A fourth example of the medical imaging device 10 of the present embodiment is as illustrated in FIG. 13, and a configuration different from that of the first to third examples will be described below. Note that components similar to those of the medical imaging device 10 according to the first example are denoted by the same reference numerals, and description thereof will be omitted.

As illustrated in FIG. 13, a medical imaging device 10C according to the fourth example includes an illumination unit 11C and an operative field camera unit 12C at positions where an illumination optical axis 11*a* and an image axis 12*a* are orthogonal to each other. In addition, the medical imaging device 10C according to the fourth example includes a reflection unit 17 that reflects the irradiation light emitted from the illumination unit 11C to coincide with the image axis 12*a* of the operative field camera unit 12C.

The reflection unit 17 is arranged between the operative field camera unit 12C and the patient as a subject, and is inclined at an angle at which the illumination light emitted from the illumination unit 11C is caused to epi-illumination coaxially with the image axis 12*a* of the operative field camera unit 12 C. The reflection unit 17 is preferably, for example, a half mirror.

Figure 14:
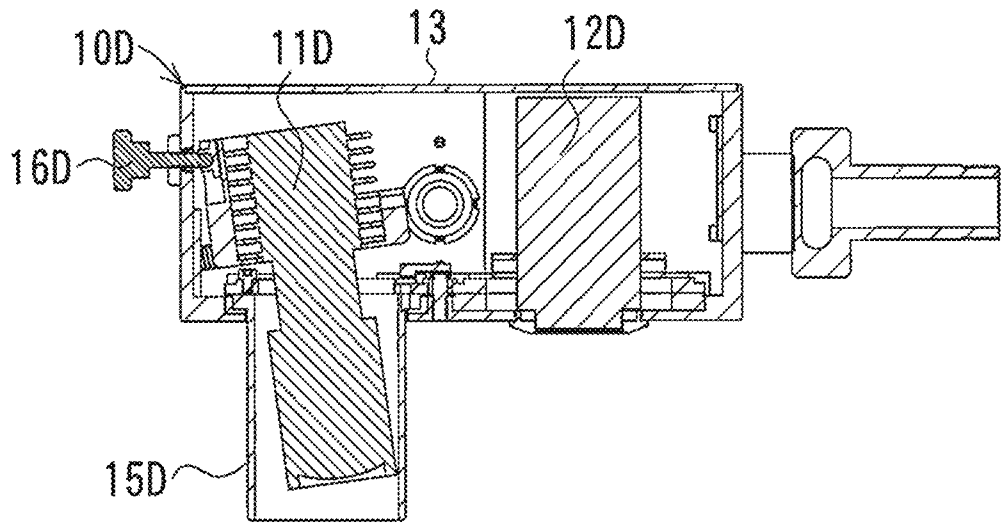
FIG. 14 is an explanatory diagram illustrating a fifth example of the medical imaging device according to the embodiment of the present invention.

A fifth example of the medical imaging device 10 of the present embodiment is as illustrated in FIG. 14, and a configuration different from that of the first to fourth examples will be described below. Note that configurations similar to those of the first example are denoted by the same reference numerals, and description thereof is omitted.

In a medical imaging device 10D according to the fifth example, an illumination unit 11D and an operative field camera unit 12D are arranged in parallel in a housing 13D.

The illumination unit 11D is housed in an adjusting unit 15D formed in a cylindrical shape, and is slightly inclined toward an image axis 12*b* side of the operative field camera unit 12D. In addition, the inclination angle of the illumination unit 11D is adjusted by operating an inclination adjusting unit 16D such that an illumination optical axis 11*a* of the illumination unit 11D coincides with the image axis 12*b* of the operative field camera unit 12D.

As illustrated in FIG. 14, the inclination adjusting unit 16D can adjust the inclination angle of the illumination unit 11D by pushing or pulling the illumination unit 11D at its distal end portion to rotate the illumination unit 11D about a rotation axis (not illustrated). The inclination adjusting unit 16D preferably has a configuration capable of adjusting the angle formed by the illumination optical axis 11*a* and an image axis 12*a* in a range of, for example, 3° or more and 6° or less according to the distance from the operative field camera unit 12D to the operative site of the patient. Note that the illumination unit 11D is constantly biased by a push spring (not illustrated) or the like to maintain the inclination.

Figure 15:
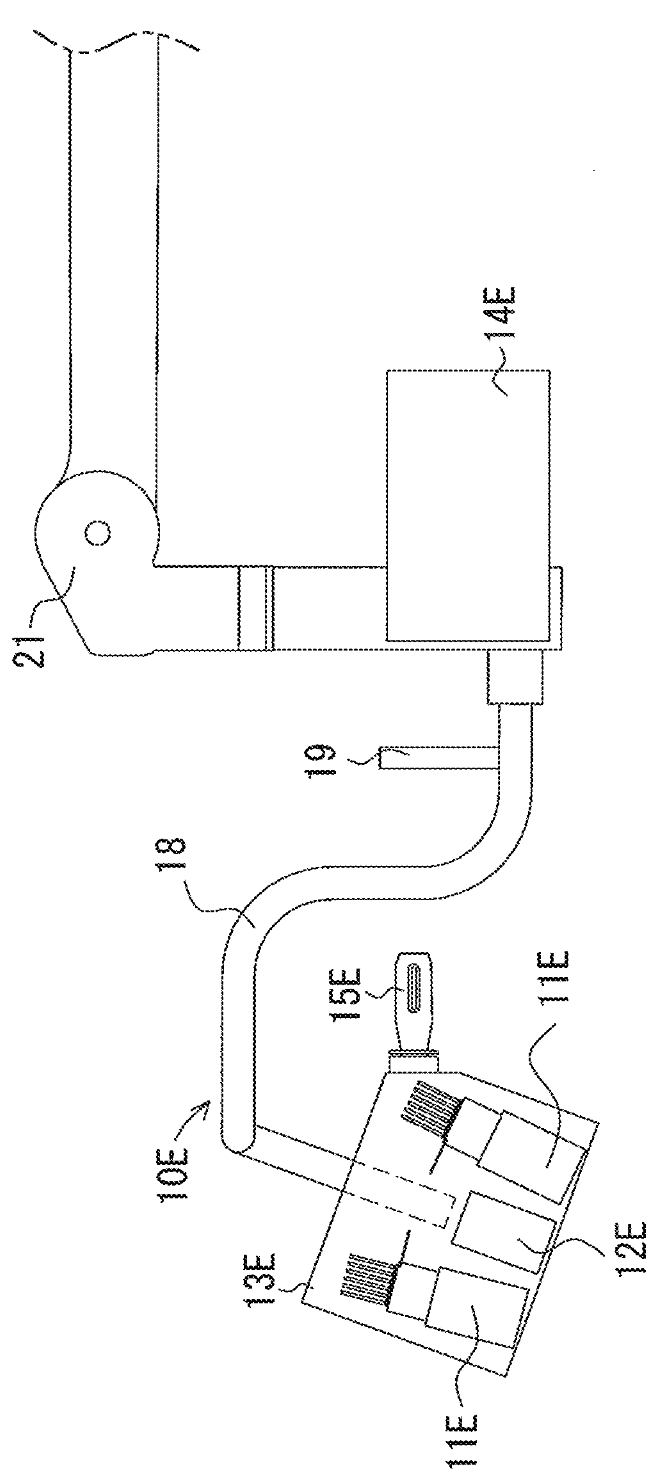
FIG. 15 is an explanatory diagram illustrating a sixth example of the medical imaging device according to the embodiment of the present invention.

A sixth example of the medical imaging device 10 of the present embodiment is as illustrated in FIG. 15, and a configuration different from that of the first to fifth examples will be described below. Note that configurations similar to those of the first example are denoted by the same reference numerals, and description thereof is omitted.

In a medical imaging device 10E according to the sixth example, a housing 13E is provided via the support arm 18 instead of the distal end of the arm unit 21. In addition, display units 14E and 14E are provided not on both side surfaces of the housing 13E but on the distal end of the arm unit 21. Note that, in FIG. 15, the illumination unit 11E and the operative field camera unit 12E provided inside the housing 13E are illustrated for convenience of description. Although only one of the display units 14E and 14E is illustrated in FIG. 15, the display unit is provided such that the display screen faces outward similarly to FIG. 4 and the like.

The housing 13E is provided with the illumination unit 11E and the operative field camera unit 12E therein, and is provided at one end of the support arm 18. Furthermore, the housing 13E is provided with an adjusting unit 15, and the inclination of the operative field camera unit 12E and the illumination unit 11 can be adjusted by the operator operating the adjusting unit 15E to adjust the inclination of the housing 13E. In addition, the operator operates the adjusting unit 15E to adjust the angle between an illumination optical axis of the illumination unit 11E and an image axis of the operative field camera unit 12E, so that the operator can adjust the position of the light field 1 to a portion where the illumination optical axis 11*a* coincides with the operative field center C (see FIG. 8(*b*)).

The display units 14E and 14E are provided adjacent to the housing 13E, and are provided at the distal end of the arm unit 21, for example. Since the display units 14E and 14E are provided separately from the housing 13E, the display units 14E and 14E are not inclined even if the operative field camera unit 12E is inclined.

The support arm 18 is formed in a shape that does not interfere with the surgery by the operator, and preferably has a shape that does not interfere with the adjusting unit 15E, the operator's hand, or the like when the operator operates the adjusting unit 15E provided in the housing 13E. The other end portion of the support arm 18 is attached to the arm unit 21 via a handle portion 19. By operating the handle portion 19, the housing 13E can be rotated as illustrated in FIG. 15. Furthermore, the handle portion 19 may include a switch unit that adjusts a focus function, a zoom function, and the like of the operative field camera unit 12E, and a switch unit that adjusts lighting and dimming of the illumination unit 11E.

A procedure for appropriately imaging the operative site of the patient by the medical imaging device 10 of the present embodiment having the above-described configuration will be described below using the medical imaging device 10 according to the first example as an example.

First, as preparation before a surgery, the operator grips the adjusting unit 15 and disposes the housing 13 at a position suitable for the operative field camera unit 12 to capture an image of the operative site of the patient and not interfering with the surgery by the operator. In a general surgery, a position obliquely above the operative field and near the shoulder of the operator about 60 cm to 90 cm away from the center of operative field is preferable.

Next, the operator operates the inclination adjusting unit 16 to adjust the angle formed by the illumination optical axis 11*a* of the illumination unit 11 and the image axis 12*a* of the operative field camera unit 12, so that the light field 11*b* on the operative field formed by the illumination unit 11 becomes clear and the operator can easily adjust the position so that the operative field center C and the light field 11*b* coincide with each other.

Furthermore, the operator rotates the adjusting unit 15 that adjusts the range and direction of the image displayed on the display units 14 and 14 while confirming the imaging condition of the operative site of the patient displayed on the display units 14 and 14, and the preparation before a surgery is completed.

Then, at the start of the surgery, the operator adjusts the position of the medical imaging device 10 such that the light field 11*b* formed by the medical imaging device 10 coincides with the operative field center C, whereby the center of operative field is appropriately imaged thereafter. In a case where the center of operative field moves with the progress of the operation, the operator can easily grasp that the center of operative field is not appropriately imaged due to the shift of the light field 11*b* of the illumination unit 11. In such a case, the operator grips the adjusting unit 15 and causes the light field 11*b* of the illumination unit 11 to coincide with the center of operative field, whereby the center of operative field can be appropriately imaged. Furthermore, in a case where it is necessary to enlarge or reduce the imaging range, the imaging at an appropriate magnification can be performed by changing the zoom of the operative field camera unit 12 while the operator, the assistant, or the like views the display units 14 and 14.

Note that the image data of the operative site of the patient captured by the operative field camera unit 12 is stored in the storage unit 42 or the like.

As described above, in the medical imaging device 10 of the present embodiment, the operative field camera unit 12 can be arranged at a position suitable for imaging the operative site of the patient and not interfering with the operation by the operator. Therefore, it is not necessary to provide a plurality of cameras, and it is possible to appropriately image the center of operative field with one camera. Furthermore, in the medical imaging device 10 of the present embodiment, the image of the operative site captured by the operative field camera unit 12 is displayed on the display units 14 and 14, so that the operator can easily confirm the image.

The invention disclosed in the present specification includes, in addition to the configurations of the respective inventions and the embodiments, those specified by changing these partial configurations to other configurations disclosed in the present specification, those specified by adding other configurations disclosed in the present specification to these configurations, or those specified by deleting these partial configurations to the extent that a partial action and effect can be obtained and forming a superordinate concept.

INDUSTRIAL APPLICABILITY

A medical imaging device according to the present invention can image an operative site of a patient at various operation sites.

REFERENCE SIGNS LIST

10, 10A, 10B, 10C, 10D, 10E medical imaging device
11, 11A, 11B, 11C, 11D, 11E illumination unit
11*a* illumination optical axis
12, 12A, 12B, 12C, 12D, 12E operative field camera unit
12*a* image axis
13, 13E housing
14, 14E display unit
15, 15E adjusting unit
16, 16A, 16D inclination adjustment unit
16*a* connecting member
17 reflection unit
18 support arm
19 handle portion
21 arm unit
22 base portion
23 surgical light
31 control unit
32 storage unit
33 transmission/reception unit
34 drive unit

The invention claimed is:

1. A medical imaging device comprising:

an illumination unit configured to spot-illuminate a center of operative field of a surgical patient;

an operative field camera unit configured to capture an image of a center of irradiation range by the illumination unit;

a housing that covers the illumination unit and the operative field camera unit; and a pair of display units attached to side surfaces of the housing and visually recognizable from both sides of the surgical patient.

2. The medical illumination imaging device according to claim 1, wherein the illumination unit includes a plurality of light sources, the plurality of light sources is arranged on a diagonal line or in a ring shape so as to surround a periphery of the operative field camera unit with the operative field camera unit as a center, and the illumination unit is provided at an angle at which an illumination optical axis of the illumination unit and an image axis of the operative field camera unit coincides with each other on the center of operative field.

3. The medical illumination imaging device according to claim 1, further comprising:

a reflection unit that reflects irradiation light emitted from the illumination unit to coincide with an image axis of the operative field camera unit.

4. The medical illumination imaging device according to claim 1, wherein the illumination unit and the operative field camera unit are arranged in parallel, and the illumination unit is installed at an angle at which an illumination optical axis of the illumination unit coincides with an image axis of the operative field camera unit arranged on the center of operative field.

5. The medical illumination imaging device according to claim 1 further comprising:

an adjusting unit configured to adjust a direction of an image displayed on the display units.

6. The medical imaging device according to claim 1, further comprising an inclination adjusting unit configured to adjust an angle formed by an illumination optical axis of the illumination unit and an image axis of the operative field camera unit, wherein the inclination adjusting unit adjusts the angle formed.

7. The medical imaging device according to claim 1, wherein the illumination unit spot-illuminates the center of operative field of the surgical patient from a position of 10 cm to 150 cm away from the operative field.

8. The medical illumination imaging device according to claim 2, further comprising:

an adjusting unit configured to adjust a direction of an image displayed on the display units.

9. The medical illumination imaging device according to claim 3, further comprising:

an adjusting unit configured to adjust a direction of an image displayed on the display units.

10. The medical illumination imaging device according to claim 4, further comprising:

an adjusting unit configured to adjust a direction of an image displayed on the display units.

11. The medical imaging device according to claim 2, further comprising an inclination adjusting unit configured to adjust an angle formed by an illumination optical axis of the illumination unit and an image axis of the operative field camera unit, wherein the inclination adjusting unit adjusts the angle formed.

12. The medical imaging device according to claim 3, further comprising an inclination adjusting unit configured to adjust an angle formed by an illumination optical axis of the illumination unit and an image axis of the operative field camera unit, wherein the inclination adjusting unit adjusts the angle formed.

13. The medical imaging device according to claim 4, further comprising an inclination adjusting unit configured to adjust an angle formed by an illumination optical axis of the illumination unit and an image axis of the operative field camera unit, wherein the inclination adjusting unit adjusts the angle formed.

14. The medical imaging device according to claim 2, wherein the illumination unit spot-illuminates the center of operative field of the surgical patient from a position of 10 cm to 150 cm away from the operative field.

15. The medical imaging device according to claim 3, wherein the illumination unit spot-illuminates the center of operative field of the surgical patient from a position of 10 cm to 150 cm away from the operative field.

16. The medical imaging device according to claim 4, wherein the illumination unit spot-illuminates the center of operative field of the surgical patient from a position of 10 cm to 150 cm away from the operative field.

* * * * *